US010264971B1

(12) United States Patent
Kennedy et al.

(10) Patent No.: US 10,264,971 B1
(45) Date of Patent: Apr. 23, 2019

(54) SYSTEM AND METHODS FOR INTEGRATING FEEDBACK FROM MULTIPLE WEARABLE SENSORS

(71) Applicant: Verily Life Sciences LLC, Mountain View, CA (US)

(72) Inventors: Scott Brian Kennedy, Mountain View, CA (US); Mark Murphy, Palo Alto, CA (US); Ali Shoeb, Mill Valley, CA (US); Nikhil Bikhchandani, San Francisco, CA (US); Hongsheng Wang, San Jose, CA (US); Emre Demiralp, San Francisco, CA (US); Anupam Pathak, Mountain View, CA (US); Tushar Parlikar, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 149 days.

(21) Appl. No.: 15/250,634

(22) Filed: Aug. 29, 2016

Related U.S. Application Data

(60) Provisional application No. 62/211,361, filed on Aug. 28, 2015.

(51) Int. Cl.
*A61B 5/00* (2006.01)
*A61B 5/11* (2006.01)
(Continued)

(52) U.S. Cl.
CPC .......... *A61B 5/0024* (2013.01); *A61B 5/0022* (2013.01); *A61B 5/0205* (2013.01);
(Continued)

(58) Field of Classification Search
CPC ... A61B 5/0024; A61B 5/0022; A61B 5/0205; A61B 5/1118; A61B 5/112;
(Continued)

(56) References Cited

U.S. PATENT DOCUMENTS 8,460,001 B1* 6/2013 Chuang .............. G09B 19/0038
434/247
2016/0007158 A1* 1/2016 Venkatraman ........ H04W 4/023
455/456.2
(Continued)

OTHER PUBLICATIONS

Zhan et al., "High Frequency Remote Monitoring of Parkinson's Disease via Smartphone: Platform Overview and Medication Response Detection", Jan. 5, 2016.
(Continued)

*Primary Examiner* — Michael Carey
(74) *Attorney, Agent, or Firm* — McDonnell Boehnen Hulbert & Berghoff LLP

(57) ABSTRACT

A system including two or more wearable devices includes at least one sensor in each device to detect signals related to the body of a wearer. User inputs, sensor outputs, or other information are used to determine an activity being performed or otherwise engaged in by the wearer and footsteps, heartbeats, discrete turns of the torso, or other events can be detected, from one or more of the sensor outputs, during a period of time that the user is engaged in the activity. A duration, amplitude, timing, mean value, or other characteristic of each such detected event can be determined, based on the sensor outputs, and used to generate a sample of clinically relevant information about the wearer. This information can then be used to determine the presence, stage, degree, progression, or other information about a disease state of the wearer or some other information about the wearer's body.

20 Claims, 12 Drawing Sheets

(51) Int. Cl.
*A61B 5/0205* (2006.01)
*A61B 5/024* (2006.01)

(52) U.S. Cl.
CPC ............. *A61B 5/112* (2013.01); *A61B 5/1118* (2013.01); *A61B 5/1121* (2013.01); *A61B 5/4082* (2013.01); *A61B 5/4842* (2013.01); *A61B 5/681* (2013.01); *A61B 5/6804* (2013.01); *A61B 5/6898* (2013.01); *A61B 5/7282* (2013.01); *A61B 5/02416* (2013.01); *A61B 5/02438* (2013.01); *A61B 2562/0219* (2013.01)

(58) Field of Classification Search
CPC ... A61B 5/1121; A61B 5/4082; A61B 5/4842; A61B 5/6804; A61B 5/681; A61B 5/6898; A61B 5/7282; A61B 5/02416; A61B 5/02438; A61B 2562/0219
USPC .................................................. 600/300, 301
See application file for complete search history.

(56) References Cited

U.S. PATENT DOCUMENTS

2016/0287940 A1* 10/2016 Balakrishnan ....... A61B 5/7246
2016/0367202 A1* 12/2016 Carter ...................... A61B 5/02

OTHER PUBLICATIONS

Yang et al., "Objective and quantitative assessment of motor function in Parkinson's disease—from the perspective of practical applications", Annals of Translational Medicine, 2016, pp. 1-8.
Tzallas et al., "Perform: A System for Monitoring, Assessment and Management of Patients with Parkinson's Disease", Sensors 2014, ISSN 1424-8220, pp. 21329-21357.
Pan et al., "A Mobile Cloud-Based Parkinson's Disease Assessment System for Home-Based Monitoring", Mar. 26, 2015.
Taylor, "Roche rolls out smartphones for continuous monitoring of participants in Parkinson's trial", FierceBiotech, Aug. 17, 2015.
Yang, "Effective Dysphonia Detection Using Feature Dimension Reduction and Kernel Density Estimation for Patients with Parkinson's Disease", PLOS ONE, vol. 9, Issue 2, Feb. 2014, pp. 1-10.
Benba et al., "Voice analysis for detecting patients with Parkinson's disease using the hybridization of the best acoustic features", International Journal on Electrical Engineering and Informatics, vol. 8, No. 1, Mar. 2016, pp. 108-116.
Mancini et al., "Continuous Monitoring of Turning in Parkinson's disease: Rehabilitation Potential", HHS Public Access Author manuscript, NeuroRehabilitation, 2015.
El-Gohary et al., "Continuous Monitoring of Turning in Patients with Movement Disability", Sensors 2014, ISSN 1424-8220, pp. 356-369.

* cited by examiner

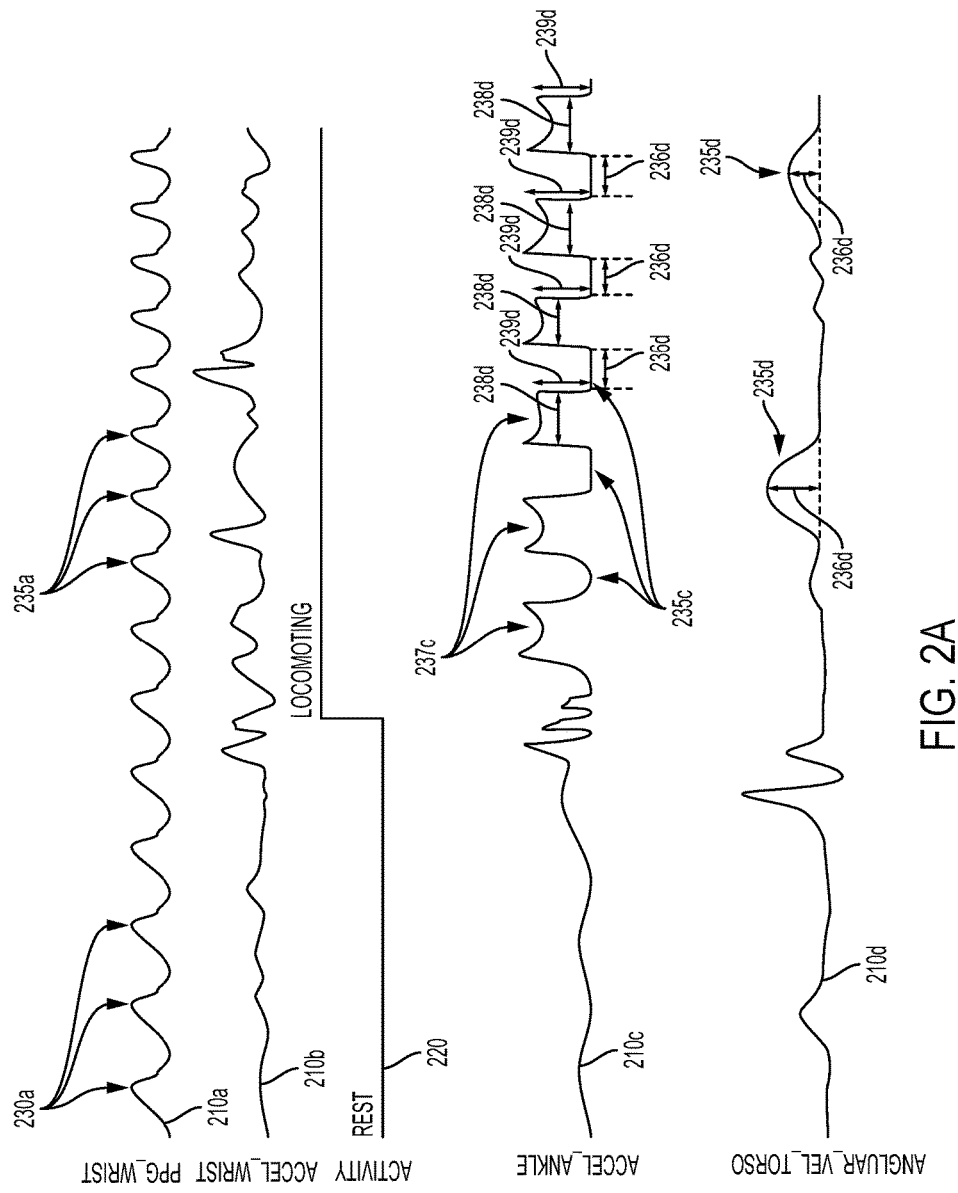

SYSTEM AND METHODS FOR INTEGRATING FEEDBACK FROM MULTIPLE WEARABLE SENSORS

CROSS-REFERENCE TO RELATED APPLICATION

This application claims priority to U.S. Provisional Patent Application No. 62/211,361, filed Aug. 28, 2015, which is hereby incorporated by reference in its entirety.

BACKGROUND

Unless otherwise indicated herein, the materials described in this section are not prior art to the claims in this application and are not admitted to be prior art by inclusion in this section.

The health or physical state of a person, or a type or degree of a disease state or process, may correlate with a variety of properties or processes of the person's body. These properties or processes may be detected and used to determine such health or disease information. For example, an amount, frequency, or other characteristics of tremor in voluntary or involuntary muscle forces produced by a person may be related to the presence or type of locomotor disease or syndrome suffered by the person (e.g., Parkinson's disease, multiple sclerosis), related to a degree or severity of the disease (e.g., to a rating on a clinical scale of disease severity/progression), and/or related to an efficacy of a treatment for the disease (e.g., to a timing of administration, dosage, or other property of a pharmaceutical treatment). Additionally or alternatively, changes in such properties or processes may be related to changes or progression of such a disease or other health state. Measured properties or processes from a particular person may be compared to population norms and/or to previously measured information from the particular person in order to diagnose a disease, determine a disease state or progression, or determine some other health information about the particular person.

Properties or processes related to a health state may be measured in a clinical setting, e.g., by a doctor or other medical professional using systems or devices (e.g., load cells, balance boards, goniometers) present in a clinical setting. Additionally or alternatively, such properties or processes may be measured in the home in order to reduce costs, increase convenience, permit a higher frequency of measurement, or to provide some other benefit.

SUMMARY

Some embodiments of the present disclosure provide a system including: (i) a first body-mountable device mountable to a first body segment of a wearer, wherein the first body-mountable device includes a first sensor; (ii) a second body-mountable device mountable to a second body segment of the wearer, wherein the second body-mountable device includes a second sensor; and (iii) a controller, wherein the controller includes a computing device. The computing device of the controller is programmed to perform operations including: (a) receiving, from the first sensor, a first signal relating to the first body segment during a period of time; (b) determining, based on the first signal, a particular activity of the wearer during the period of time; (c) receiving, from the second sensor, a second signal relating to the second body segment during the period of time; (d) determining, based on the second signal, that one or more discrete events relating to the particular activity occurred during the period of time; (e) determining, based on the second signal, a characteristic of each of the one or more discrete events; and (f) transmitting an indication of the particular activity and an indication of the determined characteristic of each of the one or more discrete events relating to the particular activity.

Some embodiments of the present disclosure provide a non-transitory computer-readable medium having stored thereon instructions executable by at least one processor to perform operations including: (i) receiving, from a first sensor in a first body-mountable device, a first signal relating to a first body segment of a wearer during a period of time; (ii) determining, based on the first signal, a particular activity of the wearer; (iii) receiving, from a second sensor in a second body-mountable device, a second signal relating to a second body segment of the wearer during the period of time; (iv) determining, based on the second signal, that one or more discrete events relating to the particular activity occurred during the period of time; (v) determining, based on the second signal, a characteristic of each of the one or more discrete events; and (vi) transmitting an indication of the particular activity and an indication of the determined characteristic of each of the one or more discrete events relating to the particular activity.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 2A illustrates example signals.

DETAILED DESCRIPTION

Figure 1A:
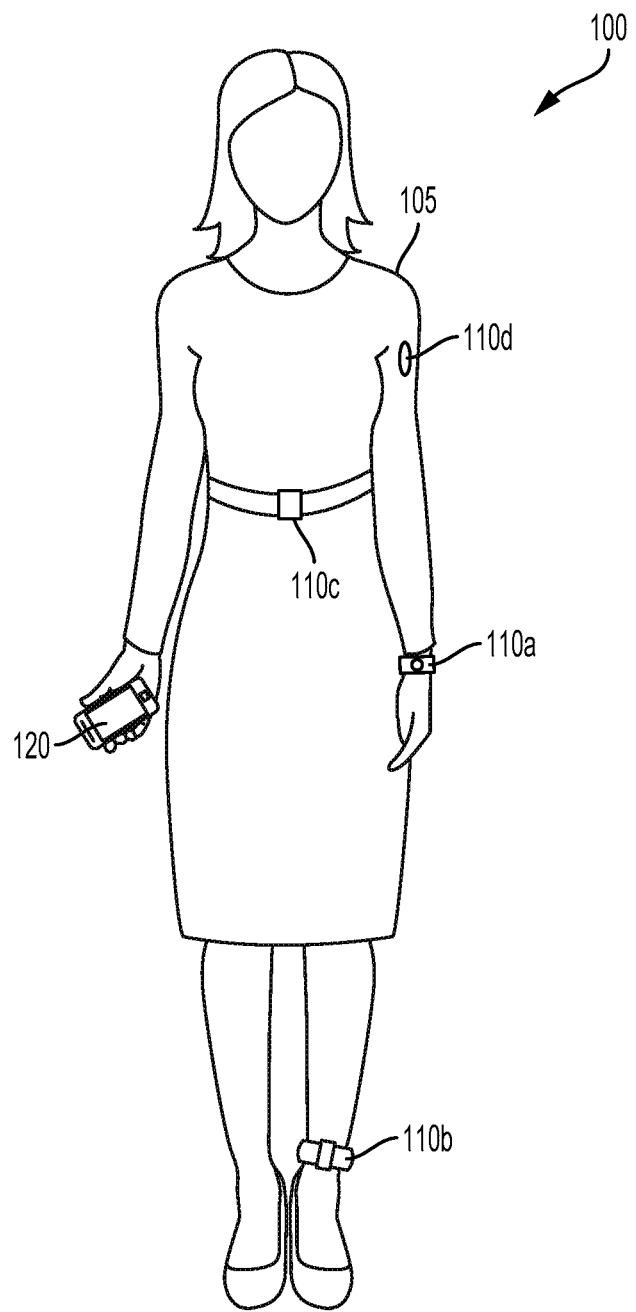
FIG. 1A illustrates body-mountable devices of an example system being worn by a wearer.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used on or in conjunction with an animal body, e.g., to generate information about the health and/or a disease state of the animal body.

I. Overview

The presence, progression, type, degree, or other properties of a disease state or process may be detected in a clinical setting by measuring one or more correlates of the disease state or process. Such correlates can include properties of body motion during a specified task (e.g., a tremor during a fine motor control task, a speed or coordination of motion during treadmill walking), properties of the cardiovascular system or other body systems at rest or in response to some specified task or activity (e.g., a heart rate or pulse timing variability at rest or during strenuous exercise), or some other measured properties. However, limiting the detection of many clinically relevant properties to a clinical environment (e.g., a doctor's office, a rehab clinic) may result in a very limited amount of disease or other health information about a person. Further, such information may be expensive to generate in terms of both medical spending and time to travel to the clinical environment and to undergo measurements. It could be beneficial to provide devices and systems to detect properties of clinical relevance outside of the clinical environment (e.g., in the home, at a person's place of work) in order to reduce the cost of such information, to increase the amount of information generated and/or to increase a temporal resolution of such information, or to provide other benefits.

A variety of wearable or otherwise body-mountable devices could be provided to measure a variety of different physical variables of a person. The devices could be worn throughout the day and/or at night to provide more clinically-relevant data, and this data can be accessed across a broader range of activities (e.g., normal walking, food preparation, engaging in other activities of daily living), times of day, or other potentially relevant conditions. A system as described herein could include multiple different devices mounted to respective different body segments, e.g., to detect properties of the different body segments. For example, a system could include devices mounted to an ankle, torso, head, or other body segment(s) of a person. Each such body-mountable device could include a single sensor (e.g., an accelerometer, a gyroscope, a temperature sensor, a photoplethysmographic sensor, an EMG sensor) or multiple sensors.

Such a system could include a controller to receive information about the body from the different body-mountable devices and/or sensors thereof. The controller could be included in one of the body-mountable devices (e.g., in a device configured to be mounted to the wrist and to provide a user interface or other functionality in addition to one or more sensors for detecting properties of the wrist). Additionally or alternatively, such a controller could be part of a cell phone or other device. The different body-mountable device and/or the controller could be in wireless communication (e.g., the body-mountable device(s) could send indications of measured properties via BLUETOOTH to a cell phone or other device that includes the controller), connected via cables, or connected in some other way.

Further, the controller and/or the body-mountable devices could be in communication with a remote server, cloud computing service, or other remote systems. Such communications could include the controller and/or body-mountable devices providing information to the remote system, e.g., signals detected from a person's body, determined characteristics of events (e.g., footsteps, heartbeats) that are present in such signals, or other information. Additionally or alternatively, the controller and/or body-mountable devices could receive information from the remote system, e.g., updates or epidemiological information, predictive models, diagnoses or other information determined based on information sent to the remote system, or other information. The controller and/or body-mountable devices could log detected or determined information and upload such information at discrete points in time and/or controller and/or body-mountable devices could continuously upload data.

Determination of useful information from one or more signals detected, by one or more body-mounted devices, from a person's body could be based on an activity being performed or otherwise engaged in by the person. Such activities could include sleeping, locomoting, walking, running, exercising, resting, cooking, typing, or some other activity. For example, if a person is walking, running, or otherwise locomoting, one or more steps taken by the person could be detected (e.g., in a signal generated by an accelerometer mounted to the person's ankle) and a total step duration, stance duration, swing duration, maximum acceleration at heel strike, or other characteristics of each step could be determined.

These determined characteristics could then be analyzed (e.g., a mean, standard deviation, or distribution of the determined characteristics could be determined) and used to diagnose a disease state, to determine a disease progression, to determine an efficacy of a drug or other treatment, or to determine some other health information, e.g., by comparing the determined characteristics to baseline data for the particular person and/or for a population of people. This analysis could include applying linear regression, nonlinear regression, a neural network, principal components analysis, or some model or process to a sample of determined characteristics from one or more sensors, body segments, days, times of day, or activity types. The determined characteristics, activities, events, health information, or other information generated by systems or methods described herein could be logged, transmitted to a remote system (e.g., via a wired or wireless link), transmitted to a user via an audio or video user interface, or used according to some other application.

An activity of a person could be determined and/or specified in a variety of ways. In some examples, a person could, via a user interface of a cell phone, body-mounted device, or other system, input an activity that the person is engaging in or input some other context information (e.g., that the person has taken a drug, that the person is about to engage in a particular diagnostic exercise). Additionally or alternatively, one or more sensors of one or more of the body-mountable devices could generate signals used to determine the activity of the person. For example, a wrist-mounted device could include a photoplethysmographic sensor and an accelerometer. A heart rate signal generated from the photoplethysmographic sensor and an acceleration signal generated by the accelerometer could be used to determine if the person is sleeping, locomoting, resting, or performing or otherwise engaging in some other activity.

Such a determined activity could then be used, as described elsewhere, to provide context for signals generated by other sensors of the wrist-mounted device or by sensors of some other devices.

It should be understood that the above embodiments, and other embodiments described herein, are provided for explanatory purposes, and are not intended to be limiting.

II. Example System of Body-Mountable Devices

Sensors disposed in one or more body-mounted devices can generate signals related to the health, disease state, or other properties of a wearer. By wearing these devices for a protracted period of time and/or while performing or otherwise engaging in a variety of different activities, the signals generated by such a system of body-mountable devices could be used to determine such properties of the wearer's body or activities. For example, such information could be used to diagnose a disease, to determine that such a disease has progressed, to determine an efficacy or dose of a drug or treatment, to predict that a particular health event (e.g., a heart attack, an incident of arrhythmia) is likely to occur, to determine the timing of a particular event (e.g., the onset or contraction of a disease), to determine the efficacy of an exercise, to determine whether a wearer is engaging in an activity correctly (e.g., performing exercise without unduly risking injury), or to determine some other information about the wearer's body.

FIG. 1A illustrates an example system 100 for detecting a variety of properties of one or more body segments of a wearer 105. The system 100 includes a number of body-mountable devices 110a, 110b, 110c, 110d and a cell phone 120. The arrangement, number, location, and other properties of the system 100, and of the body-mountable devices or other elements thereof, are intended as a non-limiting example embodiment. A system as described herein could include more or fewer body-mountable devices or other elements (e.g., could lack a cell phone, could include a base station, control pendant, or other non-body-mounted elements).

Each of the body-mountable devices 110a-d of the system 100 includes at least one sensor configured to generate a signal related to the body part to which the body-mountable device is mounted. Each body-mountable device 110a-d of the system could have the same sensor(s) or different sensors. A particular body-mountable device 110a-d could be securely mounted to a body segment (e.g., by being strapped, adhered using an adhesive, included in a tight-fitting garment, or otherwise secured to the body segment) or could be loosely mounted to a body segment (e.g., by being included in a loose-fitting garment, by being draped around a part of the wearer's 105 body).

The sensors of the body-mountable devices 110a-d could include accelerometers, gyroscopes, pressure sensors, strain sensors, magnetometers, global positioning system (GPS) receivers, photoplethysmographic sensors, laser speckle flowmeters, tonometers, blood pressure cuffs, electrocardiogram (ECG) electrodes, electromyogram (EMG) electrodes, galvanic skin resistance electrodes, thermometers, galvanic skin potential electrodes, ambient light sensors, cameras, or some other sensors or other elements. The sensors of the body-mountable devices 110a-d could be configured to generate signals related to motion (e.g., acceleration, velocity, rotation) or location (e.g., absolute location, location relative to another body segment, orientation relative to gravity) of a body segment, the temperature of a body segment, hemodynamic properties of blood and/or vasculature of the body segment (e.g., a blood flow rate, a pulse rate, a pulse timing, a pulse transit time, a blood oxygenation percent), an angle of a joint, a force exerted on the body segment (e.g., from an object, from the ground), an ambient light or temperature in the environment of the body segment, or some other properties of a body segment and/or its environment.

Body-mountable devices 110a-d, the cell phone 120, or other elements (e.g., a data logger, a controller, a communications bridge) of the system 110 could be in wired or wireless communication. For example, components of the system 100 could communicate via an ad-hoc wireless network standard (e.g., ZIGBEE). Additionally or alternatively, one or more devices of the system 100 could operate as a master, wirelessly transmitting commands to other devices of the system 100 and/or receiving information (e.g., wireless indications of signals generated by sensors of the system 100) from the other devices. In examples wherein one or more devices of the system 100 are in wired communication, power could also be provided between the devices of the system, e.g., a particular one of the devices could include a battery or other power source that could provide power to the particular one of the devices in addition to any devices in wired communication therewith.

The system 100 includes a controller that can operate to receive the signals generated by the sensors of the system 100 and facilitate some additional operations of the system 100. For example, the controller could, based on user inputs, sensor signals, or other information, determine an activity being performed or otherwise engaged in by the wearer 105 (e.g., resting, sleeping, walking, running, locomoting). The controller could detect discrete events that are taking place (e.g., footsteps, body motions, periods of rapid eye movement (REM) sleep) and/or determine characteristics of such events (e.g., the duration of a period of REM sleep, the duration of the stance phase of a footstep, the duration of a continuous period of locomotion). The controller could transmit sensor signals to a remote system (e.g., a server, a cloud computing service) and/or transmit information determined from the sensor signals (e.g., an activity of the wearer 105 at a particular point in time, detected events and/or determined characteristics thereof detected from the sensor signals, health state information determined from the event characteristics). The controller could additionally or alternatively transmit indications of such information to a wearer or other user (e.g., a physician) via an audio or video user interface element (e.g., a histogram or other visual indication of a sample of determined characteristics of a particular event detected during a particular activity, an audio or visual indication of a determined disease severity level or other determined health state).

Such a controller of the system 100 could be disposed in one of the body-mountable devices, e.g., in a wrist-mountable device 110a that may include a display, buttons, a touchscreen, or some other user interface elements. Additionally or alternatively, such a controller could be disposed in the cell phone 120 or in some other element or device of the system 100. In such an example, the cell phone 120 or other controller-bearing element of the system 100 could, itself, include one or more sensors (e.g., accelerometers, gyroscopes, GPS receivers) that could be operated to generate signals related to the wearer's 105 body, activities, or environment or related to some other properties of interest. The controller of the system 100 could be implemented as a special-purpose computing device (e.g., a microcontroller of a discrete control pendant or other device). Additionally or alternatively, elements of the controller could be implemented by a general-purpose computing device, e.g., a microprocessor of the cell phone 120. In such an example, functionality of the controller could be provided by instructions stored in a computer-readable medium (e.g., a flash memory of the cell phone 120) that could be executed by the controller. Such instructions could be provided in the form of an application that could be downloaded to the cell phone 120 (or other computing device) from the internet.

The illustrated example system 100 includes a wrist-mounted device 110a. The wrist-mounted device 110a could take the form of a watch or fitness band and could include accelerometers, gyroscopes, or other sensors to detect the motion of the wrist, forearm, hand, or other body segment(s). The wrist-mounted device 110a could also include photoplethysmographic sensors, ECG electrodes, galvanic skin response electrodes, or other sensors for generating signals related to the operation of the autonomic nervous system, heart, cardiovascular system, or other portions of the wearer's 105 body. For example, the wrist-mounted device 110a could include a photoplethysmographic sensor configured to detect an amount of blood in subsurface vasculature of the wrist as well as to detect an oxygenation state of the blood. The wrist-mounted device 110a could further include ECG electrodes.

The illustrated example system 100 includes an ankle-mounted device 110b and a torso-mounted device 110c. These devices could include accelerometers, gyroscopes, inertial measurement units, or other sensors to measure the acceleration, orientation, or other information about the motion or location of the ankle and torso, respectively, of the wearer 105. The torso-mounted device 110c could additionally include ECG electrodes to detect the electrical activity of the wearer's 105 heart, strain gauges or other strain-sensitive elements to detect the wearer's 105 breaths, or some other sensors.

The illustrated example system 100 includes a patch device 110d mounted, by an adhesive, to skin of the wearer's 105 upper arm. The patch device 110d could include a thermometer to detect the temperature of the wearer's 105 skin. The patch device 110d could additionally or alternatively include a penetrating sensor configured to detect an amount of glucose or other analytes in the wearer's 105 body (e.g., in the wearer's 105 blood) when the penetrating sensor is inserted into the surface of the wearer's 105 skin.

The system 100 could determine that the user is performing or otherwise engaged in a particular activity during one or more periods of time. Such a determination could be based on user inputs (e.g., a user indicating that they are about to perform a particular diagnostic task or exercise), on one or more signals generated by one or more sensors of the system 100, or on some other source of information (e.g., on the identity of wireless networks that are visible to the cell phone 120). Such activities could include sleeping, exercising, running, walking, locomoting, resting, cooking, typing, bathing, driving a vehicle, or some other activity.

Based on the determination that the user is, during a particular period of time, performing or otherwise engaged in a particular activity, the system 100 could detect, based on one or more signals generated by one or more sensors of the system 100, discrete events that are related to the particular activity and that occur during the particular period of time. The discrete events could be related to a disease or other health state of interest. The events could be related to actions performed or tested in a clinical environment in order to assess the health state of interest. Additionally or alternatively, it could be determined, based on sensor signals recorded from a population of wearers, that the events are related to the health state of interest. For example, to assess the presence, progression, or other properties of a movement disorder (e.g., Parkinson's disease, dystonia, essential tremor, chorea, dyskinesia, or some other movement disorder), the events could include discrete motions or actions, e.g., footsteps, turns of the wearer's body, reaches or other arm motions, or other motions or actions engaged in by the wearer 105.

Characteristics of such events could be determined and used to determine the health state of interest (e.g., to determine the presence, type, degree, severity, progression, or other properties of a movement disorder or other disease state). For example, a duration of a stance or swing phase of number of detected footsteps during locomotion, a maximum acceleration of the ankle during an number of heel strikes of the foot during locomotion, a duration of a number of REM periods during sleep, a mean velocity of a number of discrete turns of a wearer's torso during locomotion, or some other characteristics of such events and/or of other events could be determined for each of a number of detected events. Samples of such determined characteristics could be generated and used, individually or in combination, to determine a disease or other health state of a wearer.

Figure 1B:
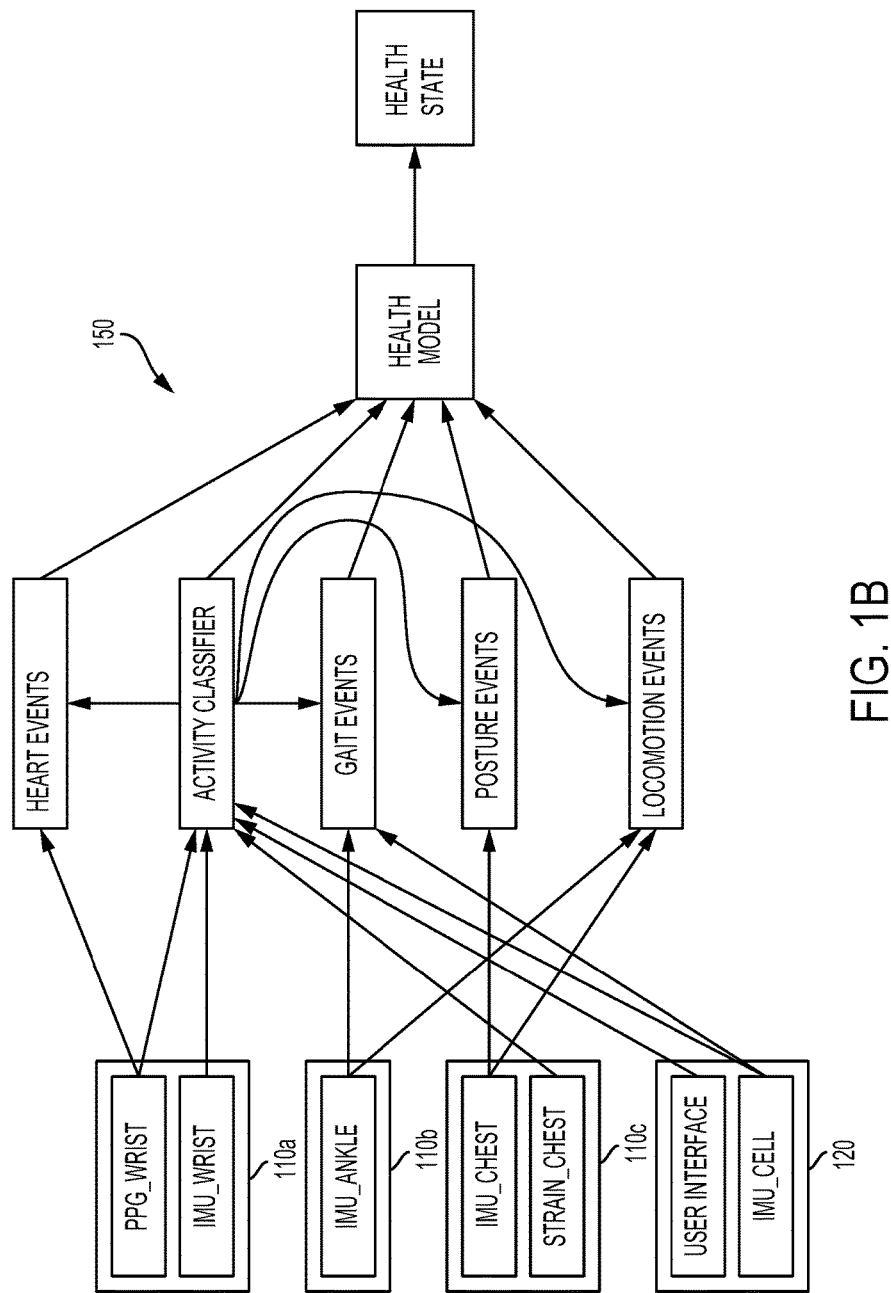
FIG. 1B illustrates a functional block diagram of elements of the example system of FIG. 1A and method of processing signals generated by sensors of the example system.

FIG. 1B is a flowchart that illustrates an example process 150 to determine, based on signals generated by sensors of the system, activities of the wearer 105, characteristics of events related to such activities, and a health state of the wearer 105 that is related to such events. Such a process 150 could be performed by a microprocessor or other computing device of the system 100 (e.g., of the cell phone 120). Sensors used in the illustrated process 150 include a photoplethysmographic sensor (PPG_WRIST) and inertial measurement unit (IMU_WRIST) in the wrist-mounted device 110a, an inertial measurement unit (IMU_ANKLE) in the ankle-mounted device 110b, a strain sensor (STRAIN_CHEST) and inertial measurement unit (IMU_CHEST) in the torso-mounted device 110c, and an inertial measurement unit (IMU_CELL) in the cell phone 120. A user interface (USER INTERFACE) of the cell phone 120 also provides information for the process 150.

An activity classifier (ACTIVITY CLASSIFIER) determines, based on a number of inputs, a particular activity of the wearer 150 during one or more periods of time. As shown in FIG. 1B, the activity classifier receives signals related to accelerations and/or rotations of the cell phone 120, the torso-mounted device 110c, and the wrist-mounted device 110a, signals related to the heart and cardiovascular system from the wrist-mounted device 110a, and information related to user inputs to the cell phone 120. However, an activity classifier could receive additional or alternative signals or other information in order to determine an activity being performed or otherwise engaged in by a wearer.

Determining an activity could include performing filtering, preprocessing, or other processes to the signals or inputs received by the activity classifier. For example, a photoplethysmographic signal could be processed to determine a pulse rate, a pulse timing, a pulse rate variability, or some other information related to an activity of the wearer. Determining an activity could include applying the signals or inputs, or signals or information determined therefrom, to a threshold, a neural network, a pattern matching algorithm, a linear or nonlinear regression, a principal components analysis, or some other function, algorithm, or process. For example, the activity classifier could determine that a wearer is resting if a determined pulse rate is below a first threshold value or that the wearer is exercising if the pulse rate is above a second threshold value.

In some examples, one or more sensors of the system 100 could be operated to generate a signal in response to detecting a particular activity, e.g., to reduce a power or bandwidth requirement of the one or more sensors when the wearer is not performing or otherwise engaged in the particular activity. This could include activating, powering, communicating with, receiving signals from, or otherwise operating a sensor in response to the determined particular activity. Additionally or alternatively, this could include increasing or otherwise changing a sampling rate, resolution, signal-to-noise ratio, amplification, or other property of the operation of a sensor in response to detecting a particular activity.

Based on the determination that a wearer is performing or otherwise engaged in a particular activity, certain events related to the particular activity can be detected from the sensors signals. The presence, timing, or other information about these events could be detected by performing a variety of operations on the sensor signals, e.g., pattern matching, convolution, filtering, domain transformation, thresholding, or some other processes to detect the presence of an event from one or more sensor signals.

For example, to detect a heartbeat, an instance of arrhythmia, or other heart-related events from a photoplethysmographic signal during a particular activity (e.g., when a wearer is engaged in strenuous exercise), a threshold could be applied to the signal in order to detect when the signal exceeds a threshold having a value related to the presence of a heartbeat in the photoplethysmographic signal. A timing, period, duration, timing variability, frequency, rate, or some other characteristic of each such detected heart event could then be determined and transmitted, logged, or used in some other manner.

In another example, to detect a wearer turning his or her body, losing balance, or other posture events from an acceleration, rotation, or other inertial signal from the torso-mounted device 110c during a particular activity (e.g., during locomotion), pattern matching could be applied to detect such events (e.g., to detect that a portion of an acceleration, rotation, or other signal corresponds to a pattern associated with such events). A maximum velocity, a mean velocity, a duration, a frequency, or some other characteristic of each such detected posture event could then be determined and transmitted, logged, or used in some other manner.

In yet another example, to detect a wearer taking a step, jumping, turning, stepping up, stopping, losing balance, or other locomotion events from an acceleration, rotation, or other inertial signal from the ankle-mounted device 110a and/or the torso-mounted device 110c during a particular activity (e.g., during locomotion), pattern matching could be applied to detect such events (e.g., to detect that a portion of an acceleration, rotation, or other signal corresponds to a pattern associated with such events). A step duration, a stance phase duration, a swing phase duration, a step length, a mean or maximum foot velocity, a step height, a frequency, a step duration variability, a mean or maximum ankle acceleration at lift-off, a mean or maximum ankle acceleration at heel strike, or some other characteristic of each such detected locomotion event could then be determined and transmitted, logged, or used in some other manner.

The process 150 also includes determining, based on one or more samples of such determined event characteristics, a health state of a wearer using a health model. Using such a health model could include determining a mean, standard deviation, distribution shape, or other properties of one or more of the samples of characteristics. The health model could apply such determined properties, or the samples themselves, to a linear regression model, a nonlinear regression model, a neural network, a principal components model, or some other model or algorithm to generate a disease severity score or other health state information. The health model could receive multiple different samples of the same characteristic from the same wearer that were generated during different periods of time, that correspond to different activities, or that differ with respect to some other consideration. For example, the health model could compare different samples of the same characteristic that were generated during different, non-overlapping periods of time in order to determine an amount of progression of a disease.

The structure, parameters, or other properties of the health model could be determined based on past information from one or more wearers, e.g., the health model could provide an output that is predictive of whether a wearer's health state is significantly different from the wearer's health state in the past and this output could be used to determine that the wearer should seek medical attention, take a drug, or pursue some other action. The health model could additionally or alternatively be based on epidemiological or other medical information about a population of persons, e.g., a population of persons that are related to a wearer according to demographics. The health model could be updated based on changes in such information, e.g., based on additional data received from a population of wearers of the devices and systems described herein.

The process 150 and/or particular elements thereof could be performed by a controller of the system 100 (e.g., a controller disposed in the cell phone 120). Additionally or alternatively, some elements of the process 150 could be performed by a remote system, e.g., by a server, cloud computing service, or other remote system that is in communication with the system 100. For example, the system 100 could transmit, to such an external system, indications of sensor signals, determined activities, determined events and/or characteristics thereof and the external system could then, based on such transmitted information, determine a health state of the wearer 105. The system 100 could additionally or alternatively receive programming, health models or parameters thereof, activity classifiers or parameters thereof, event detection models or algorithms, or some other information from such external systems and such received information could be used, by a controller of the system 100, to perform one or more elements of the process 150. Such information could be determined, by the external system, based on health information, sensor signals, or other information from the wearer 105, based on health information, sensor signals, or other information from a population of wearers, or based on some other information.

Note that the configurations and operations of sensors, controllers, or other elements of a system as described herein are meant as non-limiting examples.

III. Example Signals

FIG. 2A illustrates a number of example signals that could be received (e.g., by a controller of a system of body-mountable devices as described herein) and used to determine an activity of a wearer, to determine a health state of such a wearer, or to facilitate some other application. The example signals include a photoplethysmographic signal detected from subsurface vasculature of a wrist (210a) and a magnitude of the acceleration of the wrist (210b). The example signals also include a magnitude of the acceleration of an ankle (210c) and a magnitude of an angular velocity of a torso (210d), e.g., around the long axis of the torso. As shown in FIG. 2A, a wearer from whom the signals are detected (e.g., using body-mountable devices mounted to a wrist, ankle, and torso of the wearer) is resting during a first period of time and then and transitions to locomoting (e.g., walking, running).

One or more of the signals could be used to determine a particular activity of the wearer, e.g., to determine that the wearer is resting or locomoting. For example, the photoplethysmographic signal 210a and magnitude of the acceleration of the wrist 210b could be used to determine the activity of the wearer. This could include detecting individual heartbeat events 230a, 235a to determine a pulse rate and determining an overall power in the acceleration signal 210b. The locomoting activity could be determined if the power in the acceleration signal 210b is greater than a threshold and/or the pulse rate is greater than a threshold. This is illustrated by the activity trace 220 illustrated in FIG. 2A. Some other method could be used to determine a particular activity of the wearer based on one or more signals generated by one or more sensors.

Depending on the determined activity at a particular time, one or more discrete events can be detected in one or more of the sensor signals 210a, 210b, 210c, 210d. For example, discrete turns of the wearer's torso 235d could be detected from the magnitude of a rotational velocity of a torso 210d during the locomotion activity. Individual heartbeat events could be detected during the rest activity 230a and/or during the locomoting activity 235a. Individual footstep events, or discrete events within each footstep, could be detected during the locomotion activity. This could include detected stance phases 235c and swing phases 237c. Other events could be detecting in the illustrated signals, or in additional signals, during periods of time when a wearer is resting, locomoting, exercising, sleeping, or performing or otherwise engaged in some other activities.

For each detected event during a particular determined activity, one or more characteristics could be determined. Such characteristics could be related to a disease or to some other health state, and a sample of such determined characteristics could be used to determine information about the health state of a wearer. Such characteristics could be determined from properties of each individual detected event, from the relationship between each detected event and one or more other detected events, or based on some other property of the detected events. For example, the duration of each swing phase 238d and/or the duration of each stance phase 236d could be determined. In another example, the magnitude of the acceleration of the ankle at the end of the swing phase 239d (e.g., when the heel strikes the ground) could be determined. In yet another example, a maximum angular velocity of each discrete turn of the wearer's torso 236d could be determined, or the mean angular velocity of the wearer's torso during each such turn, or some other characteristic of turns of other events determined from the rotational velocity of the torso could be determined.

A sample of such determined characteristics of a particular event related to a particular activity (e.g., locomotion) could be determined and used to determine a health state or some other property of a wearer. Further samples of determined characteristics of different events detected in signals from different sensors, of determined characteristics of different events detected in signals from the same sensor, of determined characteristics of similar events detected in signals from the same sensor during a different event, or of some other determined characteristics could additionally be used to determine such a health state. This could include determining a mean or other statistical property of the samples and applying such a determined property to a regression model or to some other model or algorithm.

Figure 2B:
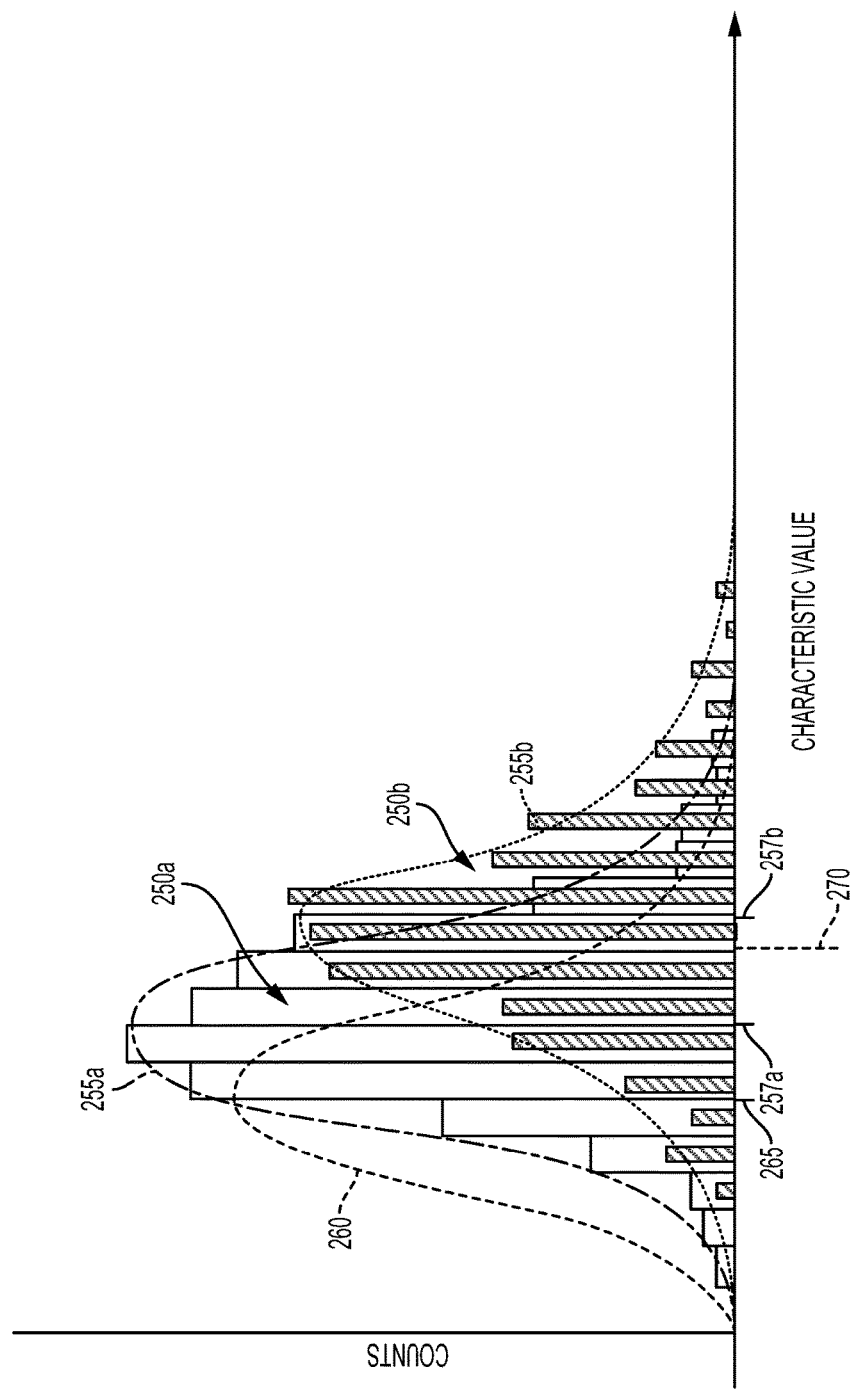
FIG. 2B illustrates example clinical data.

FIG. 2B illustrates the values of first 250a and second 250b samples of characteristics determined as described herein. The samples are illustrated as histograms, indicating the number of events detected during a particular period of time and/or when a particular activity was detected having a determined characteristic value within each of a number of discrete ranges. The two different samples 250a, 250b, could be samples of different characteristics of the same event, samples of characteristics of different events (e.g., of events detected in different sensor signals), samples of characteristics of the same event detected in the same sensor signal but associated with different activities, samples of the same characteristic of the same event and associated with the same activity but detected during different periods of time, or samples that differ with respect to some other factor(s). As shown, a mean 257a, 257b, fitted normal (or other) distribution 255a, 255b, standard deviation, or some other properties of the samples 250a, 250b could be determined, e.g., to determine the presence of a disease, the type of a disease, a severity of a disease, a degree of progression of a disease, or to determine some other health state of a wearer.

In order to determine such a health state or other information about a wearer, one or more samples of determined characteristics and/or determined properties thereof (e.g., a mean) could be applied to a linear regression model, compared to a threshold, subtracted from another sample and the difference applied to a threshold, or some other algorithm or determination could be performed. Such models, thresholds, algorithms, or parameters thereof could be determined based on samples of characteristics determined from a large population of wearers and/or based on some other information generated from a large population of individuals.

In one example, sensor signals were detected from twenty individuals and analyzed as described herein over a period of two months. The activity being performed or otherwise engaged in by the wearers was determined either based on sensor inputs (resulting in a number of samples of characteristics of 'free living' events) or based on the wearer inputting, via a user interface, an indication that they were about to engage in a specified diagnostic exercise (resulting in a number of samples of characteristics of 'structured' events). A number of characteristics of events related to activities in each of the 'free living' and 'structured' classes were determined.

The 'free living' events characteristics included, during a sleep activity, the frequency at which movement events (i.e., events where the wearer moved during sleep) were detected, the percent of sleep time during which REM occurred, and the duration of movement events. The 'free living' events also included, during a locomotion activity, the angle executed during turn events (i.e., events where the wearer engaged in a discrete turn of their body and/or torso), the duration of turn events, the maximum angular velocity during turn events, the mean angular velocity during turn events, the standard deviation of the angular velocity during turn events, the duration of the swing phase of footsteps, the duration of stance of footsteps, the total amount of time spent locomoting, and a number of other characteristics. A total of 19 characteristics were determined from 'free living' events.

The 'structured' events included the total time engaged in a mobility activity, the total amount of time engaged in standing during the mobility activity, and a number of characteristics related to locomotion during structured diagnostic exercises and to the use of a keyboard (the keyboard generating sensor signals that were used to detect and to determine characteristics of some of the 'structured' events). A total of 18 characteristics were determined from 'structured' events.

Figure 3A:
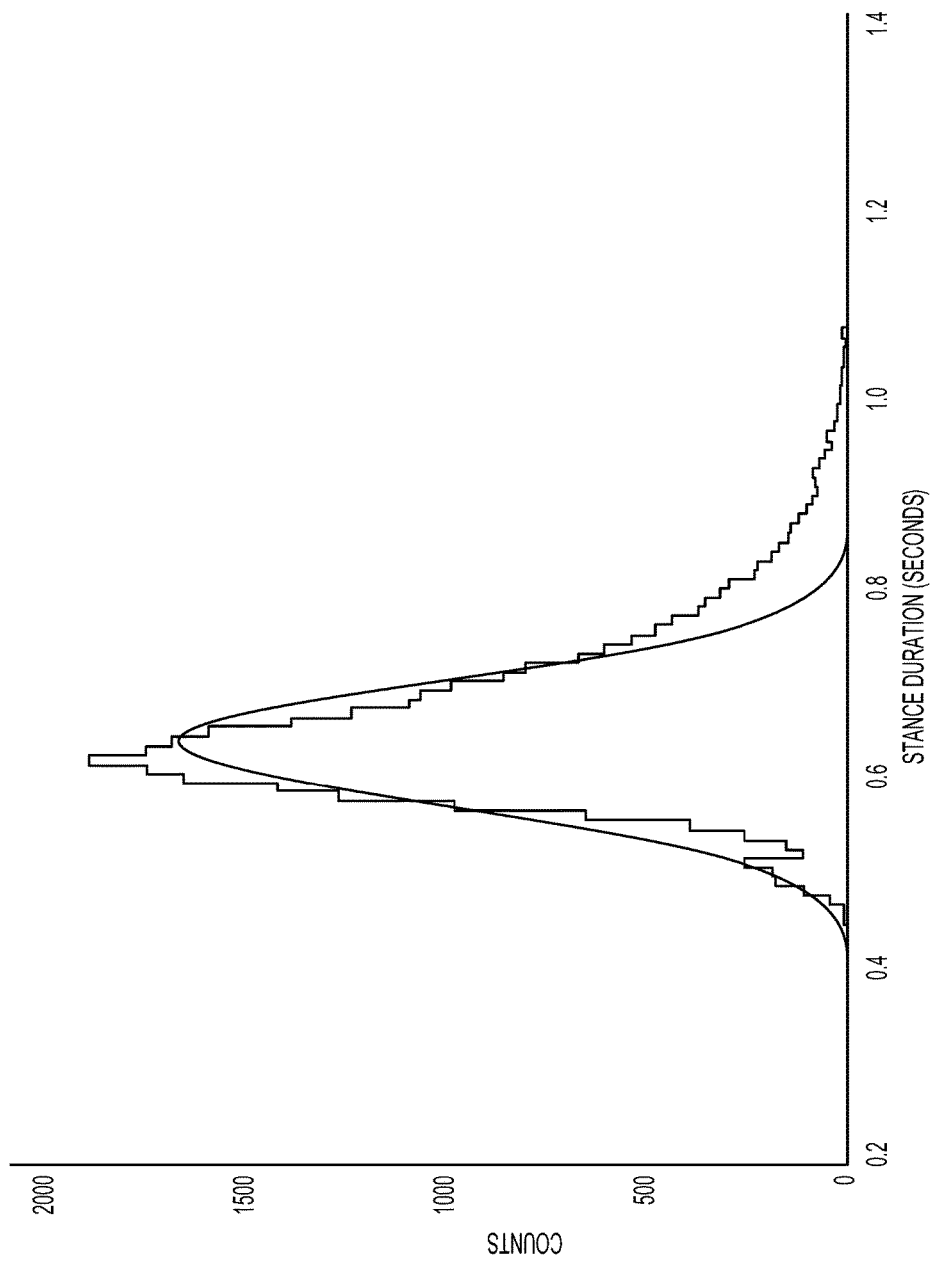
FIG. 3A illustrates example experimental data.
Figure 3B:
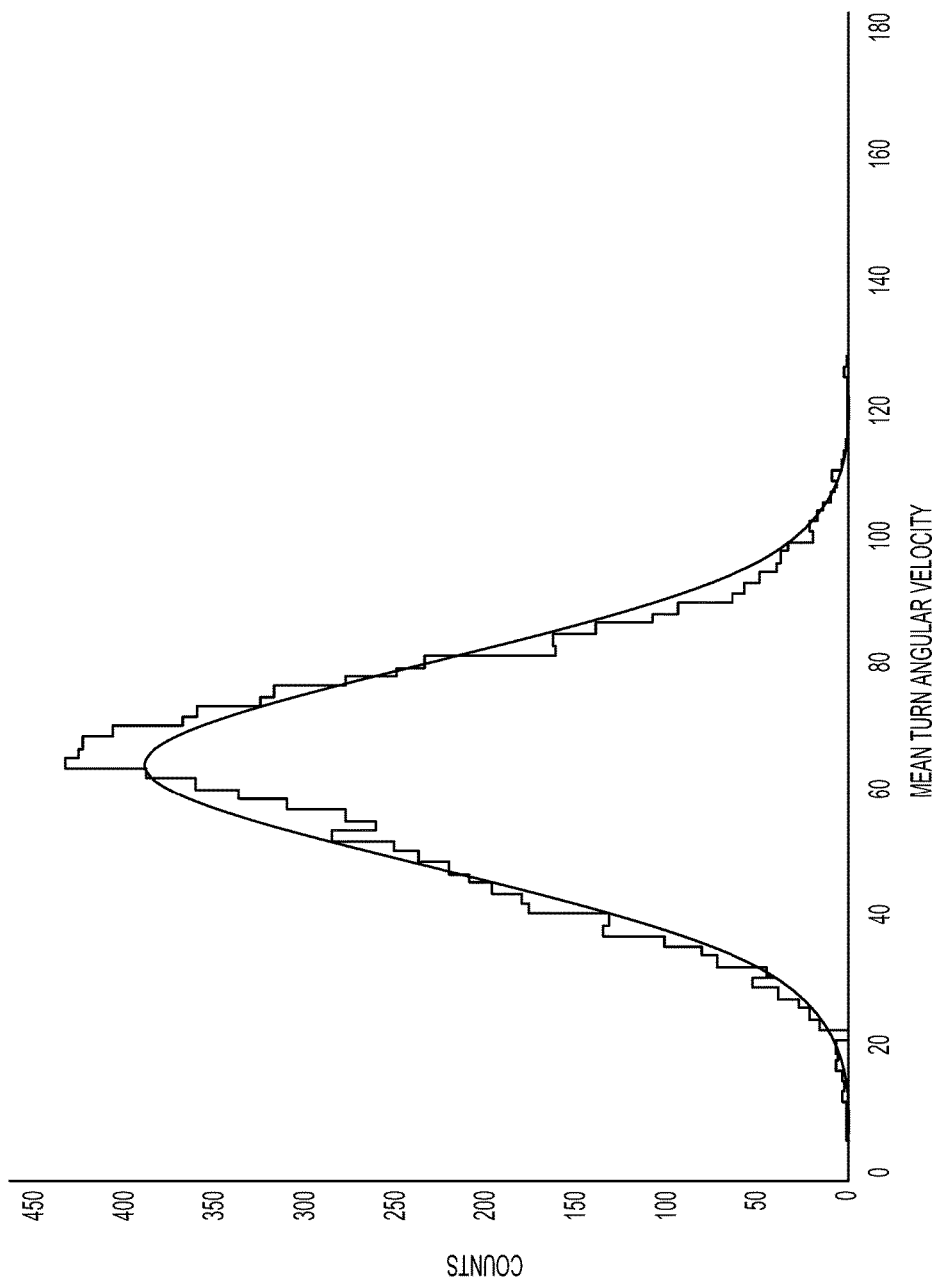
FIG. 3B illustrates example experimental data.

FIG. 3A illustrates, as a histogram, an example sample of 'stance duration' characteristics determined from stance events detected during locomotion using the systems and methods described herein. FIG. 3B illustrates, as a histogram, an example sample of 'mean angular velocity' characteristics determined from torso turn events detected during locomotion using the systems and methods described herein. The samples were generated over a period of approximately two months. Normal distributions have been fitted to each sample.

A sample of characteristics for each of the 'free living' and 'structured' events was determined for each of 20 participants in a pilot study to investigate the efficacy of the systems and methods described herein. Additionally, for each of the participants a multiple sclerosis functional composite (MSFC) score was determined based on a series of clinical evaluations performed at the beginning of the study. This MSFC score was used as a 'ground truth' to assess various different methods (including the methods described herein) for predicting the severity of each participant's multiple sclerosis symptoms.

Figure 3C:
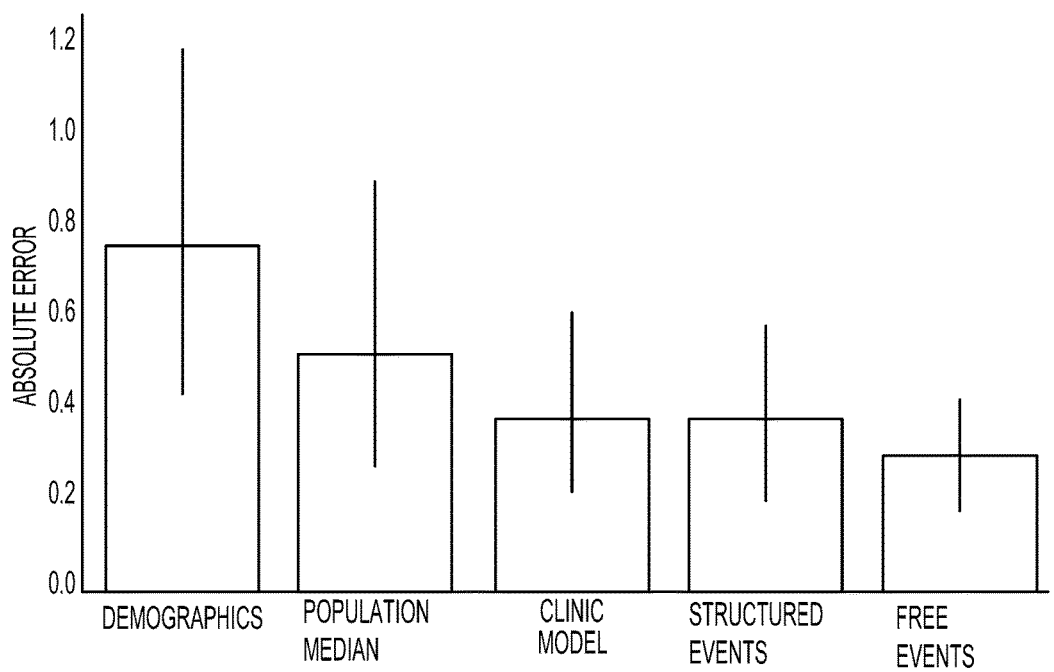
FIG. 3C illustrates the results of a statistical analysis of experimental data.

FIG. 3C illustrates the mean and standard deviation of the absolute error (i.e., the absolute value of the difference between the MSFC score for a particular participant and a predicted score determined according to each method) for each of five different methods for predicting the MSFC. For a particular participant and a particular method, a model was determined according to the particular method using data from the other 19 participants (including their MSFC scores) and used to predict the MSFC of the particular participant. So, for the first participant, the demographic data and MSFC scores of the other 19 participants were used to determine a model to predict MSFC score and the determined model was used to predict the MSFC score for the first participant. This was repeated for the other 19 participants and the mean and standard deviation of the absolute errors between the true and the predicted MSFC scores are illustrated in the box-and-whisker plot of FIG. 3C as 'DEMOGRAPHICS'.

'POPULATION MEDIAN' illustrates the ability to predict the MSFC score of a particular participant based on the median of the MSFC scores of the other 19 participants. 'CLINIC MODEL' illustrates the ability to predict the MSFC score of a particular participant based on a linear regression model, trained on data from the other 19 participants, that takes as input the results of a number of clinical measurements used to assess multiple sclerosis symptoms. 'STRUCTURED EVENTS' illustrates the ability to predict the MSFC score of a particular participant based on a linear regression model, trained on data from the other 19 participants, that takes as input the samples of characteristics determined for the 'structured' events. 'FREE EVENTS' illustrates the ability to predict the MSFC score of a particular participant based on a linear regression model, trained on data from the other 19 participants, that takes as input the samples of characteristics determined for the 'free living' events. As shown in FIG. 3C, use of a regression model based on the 'free living' events or the 'structured' events, detected and determined as described herein, resulted in MSFC predictions competitive with or superior to predictions based on clinical assessments.

IV. Example Wearable Devices

Systems as described herein can include multiple body-mountable (or wearable) devices and/or other elements (e.g., controllers, cell phones, control pendants, communications bridges). Body-mountable devices as described herein can be configured to be mounted to an external body surface of a wearer and to enable a variety of applications and functions including generating, using one or more sensors, one or more signals related to properties of a body segment to which the device is mounted. Such body-mountable devices could enable a variety of applications, including communicating with other body-mountable devices and/or controllers, determining a particular activity being performed by or otherwise engaged in by a wearer, detecting one or more events based on sensor signal(s), determining a disease severity or other health state of a wearer, or other functions.

Figure 4:
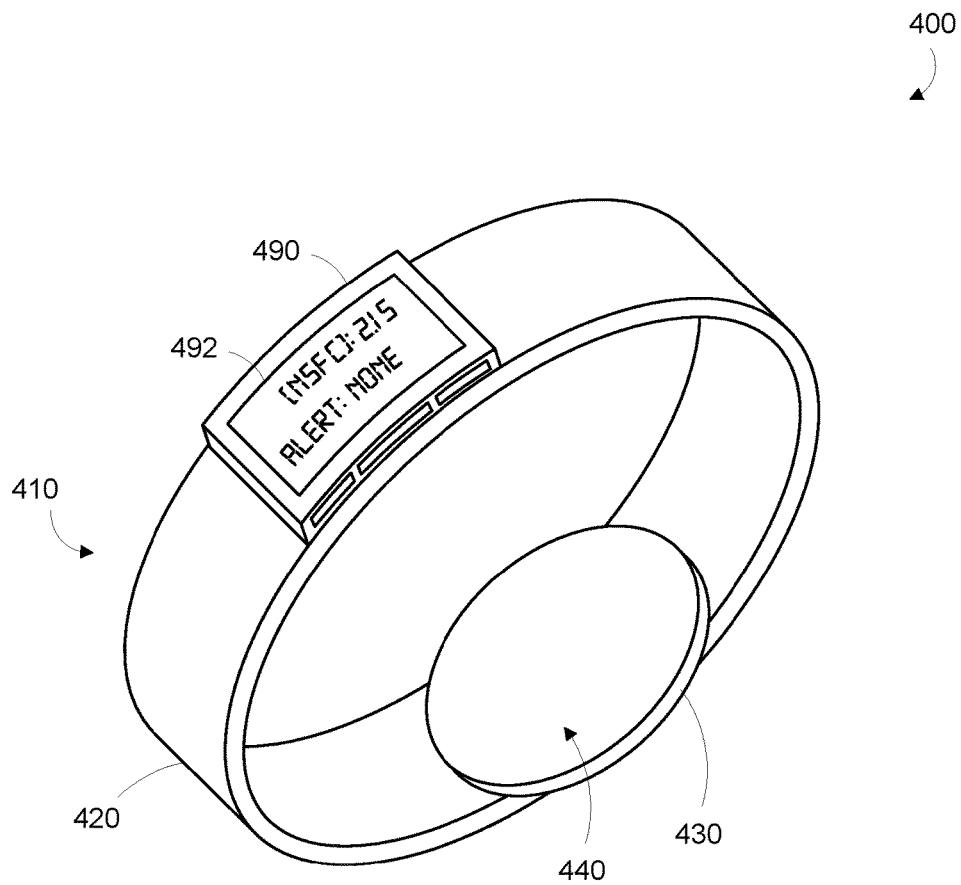
FIG. 4 is a perspective view of an example wearable device.

A body-mountable device 400 (illustrated in FIG. 4) can be configured to detect one or more properties of a body segment of a person wearing the device. The term "body-mountable device," as used in this disclosure, refers to any device that is capable of being worn at, on or in proximity to a body surface and/or body segment, such as a wrist, ankle, waist, chest, or other body part. The device may be placed in close proximity to the skin or tissue. A mount 410, such as a belt, wristband, ankle band, etc. can be provided to mount the device at, on or in proximity to the body surface. The mount 410 may prevent the wearable device from moving relative to the body to reduce measurement error and noise. In one example, shown in FIG. 4, the mount 410, may take the form of a strap or band 420 that can be worn around a part of the body. Alternatively, the mount 410 may be an adhesive substrate for adhering the wearable device 400 to the body of a wearer.

A housing 430 is disposed on the mount 410 such that it can be positioned on the body. A contact surface 440 of the housing 430 is intended to be mounted facing to the external body surface. The housing 430 may include one or more sensors for detecting one or more properties of a body segment of the wearer (e.g., hemodynamic properties of portions of subsurface vasculature, velocity, location, motion, or other kinematic information of the body segment). The housing 430 could be configured to be water-resistant and/or waterproof. That is, the housing 430 could be configured to include sealants, adhesives, gaskets, welds, transparent windows, apertures, press-fitted seams, and/or other joints such that the housing 430 was resistant to water entering an internal volume or volumes of the housing 430 when the housing 430 is exposed to water. The housing 430 could further be waterproof, i.e., resistant to water entering an internal volume or volumes of the housing 430 when the housing 430 is submerged in water. For example, the housing 430 could be waterproof to a depth of 1 meter, i.e., configured to resist water entering an internal volume or volumes of the housing 430 when the housing 430 is submerged to a depth of 1 meter. In some examples, the housing 430 could have a water resistance sufficient to satisfy an industrial standard, e.g., IPx7 as specified by the IEC 60529 Standard.

The body-mountable device 400 may also include a user interface 490 via which the wearer of the device may receive one or more recommendations, alerts, or other indications generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 490 may include a display 492 where a visual indication of an alert, recommendation, determined activity, disease state diagnosis or severity, determined health state, or other information may be displayed.

Note that example devices herein are configured to be mounted to a wrist of a wearer. However, the embodiments described herein could be applied to other body parts (e.g., an ankle, a thigh, a chest, a forehead, a thigh, a finger, a torso, an upper arm, etc.).

Wearable devices and other embodiments as described herein can include a variety of components configured in a variety of ways. Devices described herein could include electronics including a variety of different components configured in a variety of ways to enable applications of the wearable device. The electronics could include controllers, amplifiers, switches, display drivers, touch sensors, wireless communications chipsets (e.g., BLUETOOTH radios or other radio transceivers and associated baseband circuitry to enable wireless communications between the wearable device and some other system(s)), or other components. The electronics could include a controller configured to receive signals from one or more sensors (e.g., via reception of wireless indications from one or more additional body-mountable devices or other types of devices) and/or components of sensors to detect one or more properties of a body segment. The controller could include a processor configured to execute computer-readable instructions (e.g., program instructions stored in data storage of the wearable device) to enable applications of the body-mountable device. The electronics can include additional or alternative components according to an application of the body-mountable device.

Body-mountable devices as described herein could include one or more user interfaces. A user interface could include a display configured to present an image to a wearer and to detect one or more finger presses of a wearer on the interface. The controller or some other component(s) of the electronics could operate the user interface to provide information to a wearer or other user of the device and to enable the wearer or other user to affect the operation of the wearable device, to input an activity being performed or otherwise engaged in by the wearer, to determine some property of the body-mountable device and/or of the wearer of the body-mountable device (e.g., a health state of a wearer of the body-mountable device), or to provide some other functionality or application to the wearer and/or user. As one example, the wearer could press an indicated region of the user interface to indicate that the wearer is about engage in a particular diagnostic activity or exercise. Other indicated information, changes in operation of the body-mountable device, or other functions and applications of the user interface are anticipated.

Note that the embodiments illustrated in the Figures are illustrative examples and not meant to be limiting. Alternative embodiments, including more or fewer components in alternative configurations are anticipated.

Figure 5A:
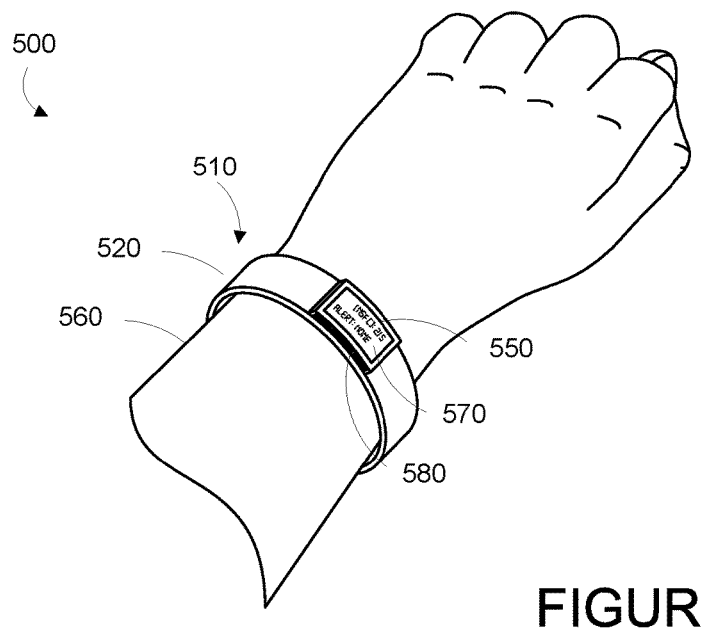
FIG. 5A is a perspective top view of an example wrist-mounted device, when mounted on a wearer's wrist.
Figure 5B:
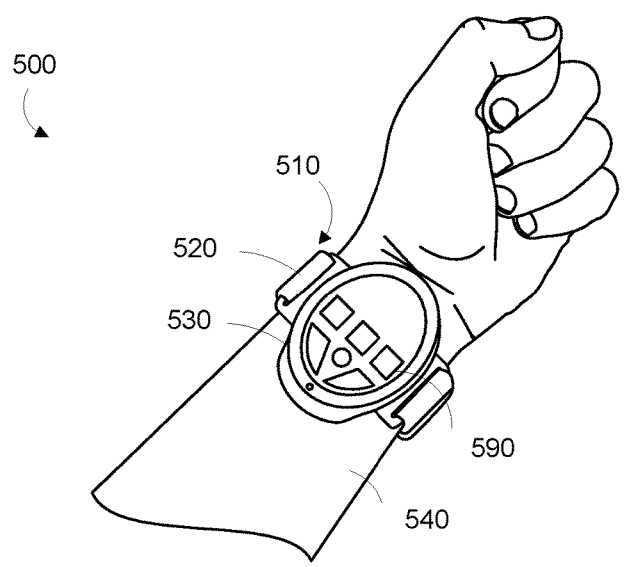
FIG. 5B is a perspective bottom view of the example wrist-mounted device shown in FIG. 5A, when mounted on a wearer's wrist.

In some examples, the body-mountable device is provided as a wrist-mounted device, as shown in FIGS. 5A and 5B. The wrist-mounted device may be mounted to the wrist of a living subject with a wristband or cuff, similar to a watch or bracelet. As shown in FIGS. 5A and 5B, the wrist mounted device 500 may include a mount 510 in the form of a wristband 520, a housing 530 containing a data collection system and positioned on the anterior side 540 of the wearer's wrist, and a user interface 550 positioned on the posterior side 560 of the wearer's wrist. The wearer of the device may receive, via the user interface 550, one or more recommendations or alerts generated either from a remote server or other remote computing device, or alerts from the measurement platform. Such a configuration may be perceived as natural for the wearer of the device in that it is common for the posterior side 560 of the wrist to be observed, such as the act of checking a wrist-watch. Accordingly, the wearer may easily view a display 570 on the user interface. Further, the housing 530 may be located on the anterior side 540 of the wearer's wrist where the subsurface vasculature or other elements of the body of the wearer may be readily observable. However, other configurations are contemplated.

The display 570 may be configured to display a visual indication of an alert, recommendation, health state, or other information. Further, the user interface 550 may include one or more buttons 580 for accepting inputs from the wearer. For example, the buttons 580 may be configured to change the text or other information visible on the display 570. As shown in FIG. 5B, housing 530 may also include one or more buttons 590 for accepting inputs from the wearer. The buttons 590 may be configured to accept inputs for controlling aspects of the data collection system, such as indicating that the wearer is engaged in a particular activity, or inputs indicating the wearer's current health state (i.e., normal, migraine, shortness of breath, heart attack, fever, "flu-like" symptoms, food poisoning, etc.).

Figure 6:
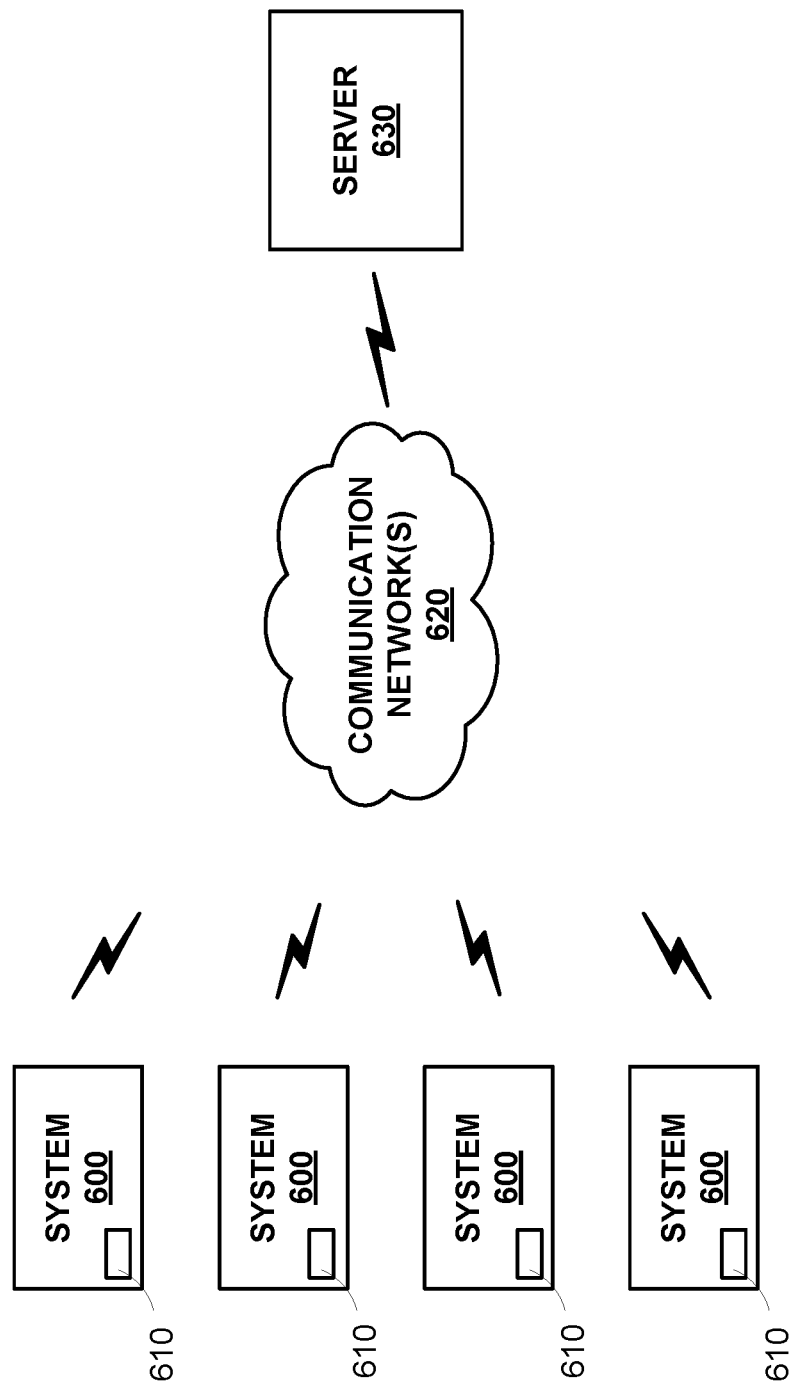
FIG. 6 is a block diagram of an example system that includes a plurality of wearable devices in communication with a server.

FIG. 6 is a simplified schematic of a numbers of systems 600 each including one or more body-mountable devices worn by, mounted to the body of, or otherwise associated with a respective wearer. The systems 600 may include a controller 610 configured to receive signals from one or more sensors of one or more body-mountable devices of each system 600. The controller 610 may additionally operate to transmit indications of the received signals, to determine a particular activity of a wearer based on one or more of the received signals, to detect one or more events and/or to determine characteristics of such events, to determine a health state of a wearer from such characteristics, to transmit indications of any or all of the above information via a communication interface (e.g., a cellular radio link, a WIFI radio link) over one or more communication networks 620 to a remote server 630. The controller 610 could be disposed in one of the body-mountable devices and/or could be disposed in some other device (e.g., a cell phone). In one embodiment, the controller 610 includes a wireless transceiver for sending and receiving communications to and from the server 630. In further embodiments, the controller 610 may include any means for the transfer of data, including both wired and wireless communications. For example, the controller may include a universal serial bus (USB) interface or a secure digital (SD) card interface. Communication networks 620 may be any one of may be one of: a plain old telephone service (POTS) network, a cellular network, a fiber network and a data network. The server 630 may include any type of remote computing device or remote cloud computing network. Further, communication network 620 may include one or more intermediaries, including, for example wherein a system 600 transmits data to a mobile phone or other personal computing device, which in turn transmits the data to the server 630.

In addition to receiving communications from the wearable device 600, such as collected sensor signals or other collected physiological properties and data regarding health state as input by the user and/or one or more properties of a wearer detected using sensors disposed in body-mountable devices of the system 600, the server may also be configured to gather and/or receive either from the system 600 or from some other source, information regarding a wearer's overall medical history, environmental factors and geographical data. For example, a user account may be established on the server for every wearer that contains the wearer's medical history. Moreover, in some examples, the server 630 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the system of body-mountable devices may be configured to determine and/or provide an indication of its own location. For example, a system of body-mountable devices may include a GPS system so that it can include GPS location information (e.g., GPS coordinates) in a communication to the server. As another example, a system of body-mountable devices may use a technique that involves triangulation (e.g., between base stations in a cellular network) to determine its location. Other location-determination techniques are also possible.

The server may also be configured to make determinations regarding the efficacy of a drug or other treatment based on information regarding the drugs or other treatments received by a wearer of the devices. From this information, the server may be configured to derive an indication of the effectiveness of the drug or treatment. If a wearer is prescribed a drug intended to treat the symptoms of multiple sclerosis, but the server receives data from the system of body-mountable devices indicating that the wearer's symptoms have been increasing over a certain number of measurement periods, the server may be configured to derive an indication that the drug is not effective for its intended purpose for this wearer.

Further, some embodiments of the system may include privacy controls which may be automatically implemented or controlled by the wearer of the device. For example, where a wearer's collected health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a system of body-mountable devices may be provided with an opportunity to control whether or how the system collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state properties, collected from his or her device may only be used for generating an individual baseline and recommendations in response to collection and comparison of his or her own data and may not be used in generating a population baseline or for use in population correlation studies.

V. Example Electronics

Figure 7:
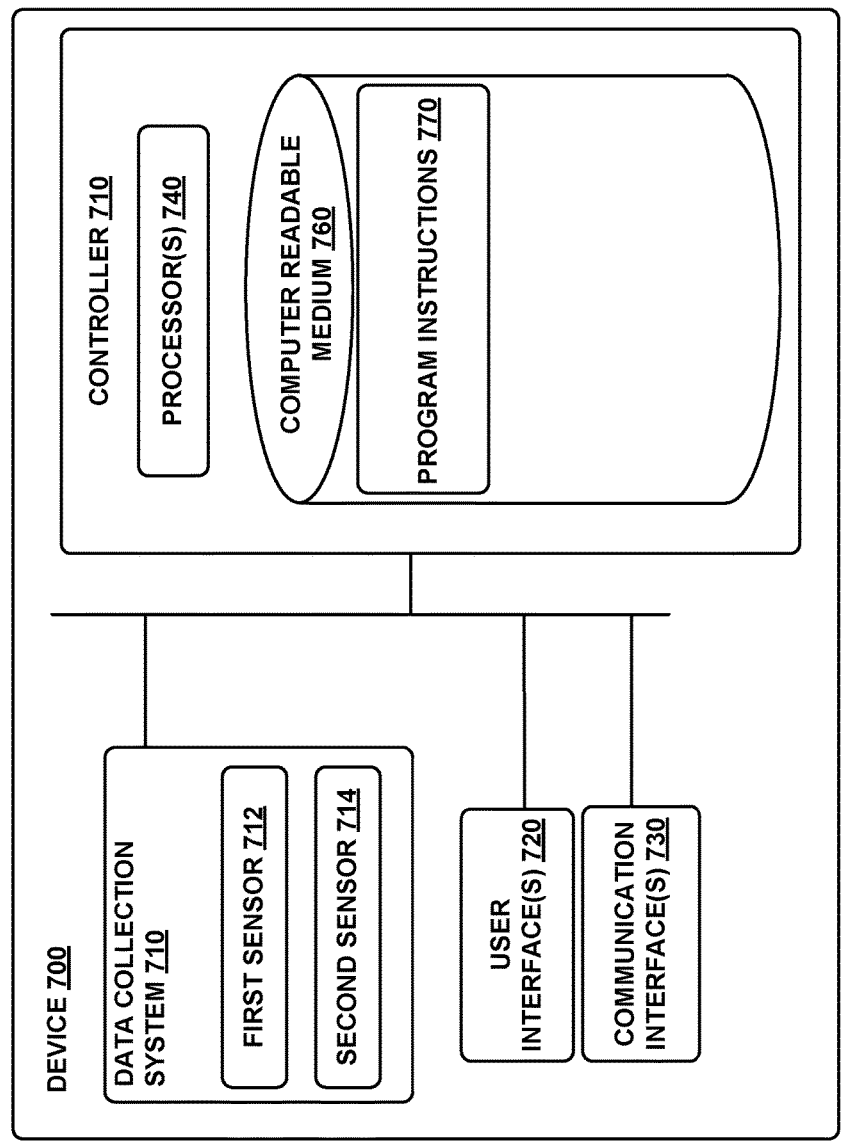
FIG. 7 is a functional block diagram of an example device.

FIG. 7 is a simplified block diagram illustrating the components of a device 700, according to an example embodiment. Device 700 may take the form of or be similar to one of the body-mountable devices 110a, 110b, 110c, 110d, 400, 500 shown in FIGS. 1A, 1B, 4, and 5A-B. However, device 700 may also take other forms, such as an ankle, waist, or chest-mounted device. Device 700 could also take the form of a device that is not configured to be mounted to a body. For example, device 700 could take the form of a cell phone, control pendant, communications bridge, or other device. Device 700 also could take other forms.

In particular, FIG. 7 shows an example of a device 700 having a data collection system 710 that includes two sensors 712, 714, a user interface 720, communication interface 730 for communicating with another system (e.g., one or more other body-mountable devices, a cell phone or other controller device), and a controller 710. The components of the device 700 may be disposed on a mount or on some other structure for mounting the device to enable stable detection of one or more properties (e.g., velocity, acceleration, force) of body segment of a wearer of the device 700, for example, mounting to an external body surface where one or more portions of subsurface vasculature or other anatomical elements are readily observable.

Controller 710 may be provided as a computing device that includes one or more processors 740. The one or more processors 740 can be configured to execute computer-readable program instructions 770 that are stored in the computer readable data storage 760. The program instructions 770 are executable by the one or more processors 740 to provide the functionality of a device 700 described herein, including any of the methods described herein.

The computer readable medium 760 may include or take the form of one or more non-transitory, computer-readable storage media that can be read or accessed by at least one processor 740. The one or more computer-readable storage media can include volatile and/or non-volatile storage components, such as optical, magnetic, organic or other memory or disc storage, which can be integrated in whole or in part with at least one of the one or more processors 740. In some embodiments, the computer readable medium 760 can be implemented using a single physical device (e.g., one optical, magnetic, organic or other memory or disc storage unit), while in other embodiments, the computer readable medium 760 can be implemented using two or more physical devices.

Sensors 712, 714 could include any components configured to detect properties and/or some other information about a body segment of a wearer as described elsewhere herein. The sensors 712, 714 could include accelerometers, gyroscopes, strain gauges, ambient light sensors, GPS receivers, temperature sensors, energy sensors, electromagnetic sensors, light sensors, chemical sensors, acoustical sensors, infrared sensors, ultraviolet sensors, tonometers, electrocardiogram electrodes, tissue impedance electrodes, or other types of sensors. The sensors 712, 714 could include photodetectors (e.g., light detectors, color detectors, polarity detectors, infrared detectors, ultraviolet detectors, cameras). In some examples, one or more of the sensors 712, 714 could include energy emitters (e.g., light emitters, heaters, acoustical transducers, current sources, voltage sources) configured to enable detection of some property of a body of a wearer (e.g., of a portion of subsurface vasculature of the wearer) by illuminating, heating, injecting a current into, applying a voltage to, or otherwise introducing an energy to the one or more portions of the body of the wearer. For example, the sensors 712, 714 could include one or more Doppler ultrasonography probes. In some examples, the sensors 712, 714 could include active optical sensors configured to illuminate a portion of subsurface vasculature and/or blood therein and the detect light responsively emitted from the portion of subsurface vasculature. Such sensors could include laser Doppler flowmeters, dynamic laser speckle sensors, photoplethysmographic sensors, fluorescence imagers, or some other active and/or passive optical sensors.

The program instructions 770 stored on the computer readable medium 760 may include instructions to perform any of the methods described herein (e.g., the methods described with reference to FIG. 8).

The program instructions 770 can also include instructions for operating a user interface 720. For example, program instructions 770 may include instructions for displaying data collected by the data collection system 710 and analyzed by the controller 710, or for displaying one or more alerts. Program instructions 770 may include instructions for displaying data related to a determined health state of a wearer. Further, program instructions 770 may include instructions to execute certain functions based on inputs accepted by the user interface 720, such as inputs accepted by one or more buttons disposed on the user interface.

Communication interface 730 may also be operated by instructions within the program instructions 770, such as instructions for sending and/or receiving information via a wireless antenna, which may be disposed on or in the device 700. The communication interface 730 can optionally include one or more oscillators, mixers, frequency injectors, etc. to modulate and/or demodulate information on a carrier frequency to be transmitted and/or received by the antenna. In some examples, the device 700 is configured to indicate an output from the processor by modulating an impedance of the antenna in a manner that is perceivable by a remote server or other remote computing device.

The program instructions 770 may, in some examples, be stored in a computer-readable medium and executed by a processor located external to the device 700. For example, the device 700 could be configured to generate and/or receive sensor signals and then transmit the data to a remote server, which may include a mobile device, a personal computer, the cloud, or any other remote system, for further processing.

The computer readable medium 760 may further contain other data or information, such as medical and health history of a user of the device 700, that may be useful in determining whether a medical condition or some other specified condition is indicated. Further, the computer readable medium 760 may contain data corresponding to certain physiological parameter baselines, above or below which a medical condition is indicated. The baselines may be pre-stored on the computer readable medium 760, may be transmitted from a remote source, such as a remote server, or may be generated by the device 700 itself. The program instructions 770 may include instructions for generating individual baselines for the user of the device 700 based on data collected over a certain number of measurement periods. Baselines may also be generated by a remote server and transmitted to the device 700 via communication interface 730. The program instructions 770 may also, upon determining that a medical or other emergency condition is indicated, generate one or more recommendations for the user of the device 700 based, at least in part, on consultation of a clinical protocol. Such recommendations may alternatively be generated by the remote server and transmitted to the device 700.

In some examples, the collected baseline profiles, determined health state information, and generated recommendations and clinical protocols may additionally be input to a cloud network and be made available for download by a user's physician. Trend and other analyses may also be performed on the collected data, such as health state information, in the cloud computing network and be made available for download by physicians or clinicians.

Further, health state data from individuals or populations of device users may be used by physicians or clinicians in monitoring efficacy of a drug or other treatment. For example, high-density, real-time data may be collected from a population of device users who are participating in a clinical study to assess the safety and efficacy of a developmental drug or therapy. Such data may also be used on an individual level to assess a particular wearer's response to a drug or therapy. Based on this data, a physician or clinician may be able to tailor a drug treatment to suit an individual's needs.

VI. Example Methods

Figure 8:
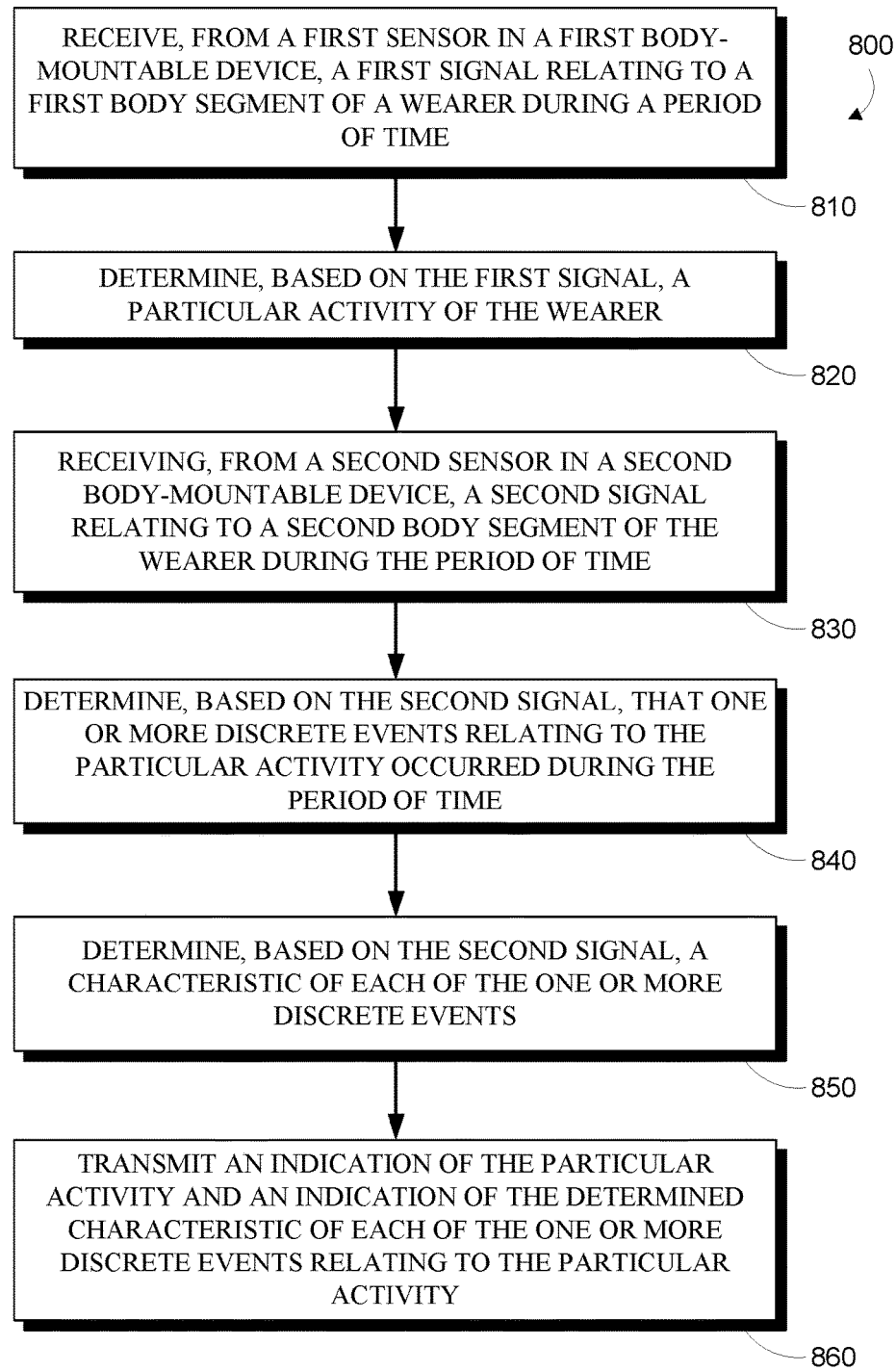
FIG. 8 is a flowchart of an example method.

FIG. 8 is a flowchart of a method 800. The method 800 could be performed by a controller of a system as described herein. Such a controller could be disposed in a body-mountable device. Such a controller could include one or more processors that could execute instructions stored in a computer readable medium, where the instructions could cause the one or more processors to perform the method 80 when executed by the one or more processors.

The method 800 includes receiving, from a first sensor in a first body-mountable device, a first signal relating to a first body segment of a wearer during a period of time (810). This could include receiving, via a wireless receiver, a wireless indication of the first signal from the first body-mountable device. Alternatively, the controller could be disposed within the first body-mountable device and receiving the first signal (810) could include receiving the first signal via a wire, cable, trace, optical fiber, of other signal-conducting means of the first body-wearable device. Receiving the first signal (810) could include powering up and/or instructing the first sensor to operate to generate the first signal.

The method 800 further includes determining, based on the first signal, a particular activity of the wearer (820). This could include determining a sleep activity, a rest activity, an exercise activity, a locomotion activity, a specified diagnostic activity, a cooking activity, or some other activity. Determining the particular activity could include performing some filtering, transformation, thresholding, pattern matching, or other processes on the first signal. For example, determining the particular activity (820) could include detecting one or more heartbeats in a photoplethysmographic signal or in some other cardiovascular signal or determining a pulse rate, a pulse timing, a pulse rate variability, or some other information from the first signal.

The method 800 further includes receiving, from a second sensor in a first body-mountable device, a second signal relating to a first body segment of a wearer during the period of time (830). This could include receiving, via a wireless receiver, a wireless indication of the second signal from the second body-mountable device. Alternatively, the controller could be disposed within the second body-mountable device and receiving the second signal (830) could include receiving the second signal via a wire, cable, trace, optical fiber, of other signal-conducting means of the second body-wearable device. Receiving the second signal (830) could include powering up and/or instructing the second sensor to operate to generate the first signal. In some examples, receiving the second signal (830) could be performed in response to determining the particular activity of the wearer (820).

The method 800 further includes determining, based on the second signal, that one or more discrete events relating to the particular activity occurred during the period of time (840). This could include filtering, transforming, or otherwise preprocessing the second signal. Determining that one or more discrete events relating to the particular activity have occurred (84) could include applying a threshold, performing pattern matching, convolving the second signal with a kernel, or performing some other process or algorithm to detect the presence, timing or, other information about the events during the period of time.

The method 800 further includes determining, based on the second signal, a characteristic of each of the one or more discrete events (850). This could include determining a maximum, a minimum, a mean, a standard deviation, a duration, a derivate, an integral, or some other property of the second signal during a period of time proximate each event.

The method 800 further includes transmitting an indication of the particular activity and an indication of the determined characteristic of each of the one or more discrete events relating to the particular activity (860). This could include generating a wireless transmission to a server, cloud computing service, or other remote system using, e.g., a cellular radio, a WIFI radio, a ZIGBEE radio, a BLUETOOTH radio, an ultrasonic or otherwise configured acoustical transceiver, or some other wireless signaling means. In another example, transmitting an indication (860) could include transmitting a signal via a wire, cable, or other wired connection. In some examples, transmitting an indication (860) could include transmitting, via one or more user interface components, an audio or visual indication that could be perceived by a wearer or by some other user.

The method 800 for operating a wearable device could include additional or alternative steps. In some examples, the method 800 could include determining a health state of the wearer based on based on the particular activity and the determined characteristic of each of the one or more discrete events relating to the particular activity. In some examples, determining a health state of the wearer could include generating multiple samples of characteristics (e.g., characteristics of events related to different activities, generated during different periods of time, or differing with respect to some other factor) and using a linear regression model, a nonlinear regression model, a neural network, or some other model or algorithm to determine the health state of the wearer.

The example method 800 illustrated in FIG. 8 is meant as an illustrative, non-limiting example. Additional or alternative elements of the method and additional or alternative components of the wearable device are anticipated, as will be obvious to one skilled in the art.

VII. Conclusion

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A system comprising:
   a first body-mountable device mountable to a first body segment of a wearer, wherein the first body-mountable device comprises a first sensor;
   a second body-mountable device mountable to a second body segment of the wearer, wherein the second body-mountable device comprises a second sensor; and
   a controller, wherein the controller comprises a computing device programmed to perform operations comprising:
      receiving, from the first sensor, a first signal relating to the first body segment during a period of time;
      determining, based on the first signal, a particular activity of the wearer during the period of time;
      receiving, from the second sensor, a second signal relating to the second body segment during the period of time;
      determining, based on the second signal and the determined particular activity of the wearer during the period of time, that one or more discrete events relating to the particular activity occurred during the period of time, wherein the one or more discrete events comprise at least one of an individual footstep taken by the wearer, a discrete turn of the wearer's torso, or an individual interaction between the second sensor and a finger of the wearer;

determining, based on the second signal, a characteristic of each of the one or more discrete events; and transmitting an indication of the particular activity and an indication of the determined characteristic of each of the one or more discrete events relating to the particular activity.

2. The system of claim 1, wherein the operations further comprise:

determining, based on the particular activity and the determined characteristic of each of the one or more discrete events relating to the particular activity, a health state of the wearer, wherein transmitting an indication of the particular activity and an indication of the determined characteristic of each of the one or more discrete events relating to the particular activity comprises transmitting an indication of the determined health state of the wearer.

3. The system of claim 2, wherein the second sensor comprises at least one of an accelerometer or a gyroscope, and wherein determining a health state of the wearer comprises determining, based on the particular activity and the determined characteristic of each of the one or more discrete events relating to the particular activity, at least one of a presence, a type, a degree of severity, or a degree of progression of a movement disorder.

4. The system of claim 1, wherein the operations further comprise:

determining, based on the particular activity and the determined characteristic of each of the one or more discrete events relating to the particular activity, at least one of a presence, a type, a degree of severity, or a degree of progression of a disease, wherein transmitting an indication of the particular activity and an indication of the determined characteristic of each of the one or more discrete events relating to the particular activity comprises transmitting an indication of the determined presence, type, degree of severity, or degree of progression of the disease.

5. The system of claim 1, wherein the first sensor comprises a photoplethysmographic sensor, and wherein determining that a wearer is engaged in a particular activity comprises determining at least one of a pulse rate or a pulse timing based on the first signal.

6. The system of claim 1, wherein the particular activity of the wearer is locomotion, and wherein the second sensor comprises at least one of an accelerometer or a gyroscope.

7. The system of claim 6, wherein the second body segment is an ankle of the wearer, wherein the one or more discrete events comprise one or more individual footsteps taken by the wearer, and wherein determining a characteristic of each of the one or more discrete events comprises determining a duration of each of the one or more individual footsteps taken by the wearer.

8. The system of claim 6, wherein the second body segment is a torso of the wearer, wherein the one or more discrete events comprise one or more discrete turns of the wearer's torso, and wherein determining a characteristic of each of the one or more discrete events comprises determining a mean angular velocity of each of the one or more discrete turns of the wearer's torso.

9. The system of claim 1, wherein the first body-mountable device comprises a transceiver, wherein the controller is disposed within the first body-mountable device, and wherein receiving, from the second sensor, the second signal relating to the second body segment comprises receiving a wireless indication of the second signal via the transceiver.

10. The system of claim 1, further comprising a third device, wherein the third device comprises a transceiver, wherein the controller is disposed within the third device, wherein receiving, from the first sensor, the first signal relating to the first body segment comprises receiving a wireless indication of the first signal via the transceiver, and wherein receiving, from the second sensor, the second signal relating to the second body segment comprises receiving a wireless indication of the second signal via the transceiver.

11. The system of claim 1, wherein receiving, from the second sensor, the second signal relating to the second body segment during the period of time is performed responsive to determining the particular activity of the wearer.

12. A non-transitory computer-readable medium having stored thereon instructions executable by at least one processor to perform operations comprising:

receiving, from a first sensor in a first body-mountable device, a first signal relating to a first body segment of a wearer during a period of time;

determining, based on the first signal, a particular activity of the wearer;

receiving, from a second sensor in a second body-mountable device, a second signal relating to a second body segment of the wearer during the period of time;

determining, based on the second signal and the determined particular activity of the wearer during the period of time, that one or more discrete events relating to the particular activity occurred during the period of time, wherein the one or more discrete events comprise at least one of an individual footstep taken by the wearer, a discrete turn of the wearer's torso, or an individual interaction between the second sensor and a finger of the wearer;

determining, based on the second signal, a characteristic of each of the one or more discrete events; and transmitting an indication of the particular activity and an indication of the determined characteristic of each of the one or more discrete events relating to the particular activity.

13. The non-transitory computer-readable medium of claim 12, wherein the operations further comprise:

determining, based on the particular activity and the characteristic of each of the one or more discrete events relating to the particular activity, a health state of the wearer, wherein transmitting an indication of the particular activity and an indication of the determined characteristic of each of the one or more discrete events relating to the particular activity comprises transmitting an indication of the determined health state of the wearer.

14. The non-transitory computer-readable medium of claim 13, wherein the second sensor comprises at least one of an accelerometer or a gyroscope, and wherein determining a health state of the wearer comprises determining, based on the particular activity and the determined characteristic of each of the one or more discrete events relating to the particular activity, at least one of a presence, a type, a degree of severity, or a degree of progression of a movement disorder.

15. The non-transitory computer-readable medium of claim 12, wherein the operations further comprise:

determining, based on the particular activity and the determined characteristic of each of the one or more discrete events relating to the particular activity, at least one of a presence, a type, a degree of severity, or a degree of progression of a disease, wherein transmitting an indication of the particular activity and an indication of the determined characteristic of each of the one or more discrete events relating to the particular activity comprises transmitting an indication of the determined presence, type, degree of severity, or degree of progression of the disease.

16. The non-transitory computer-readable medium of claim 13, wherein the first sensor comprises a photoplethysmographic sensor, and wherein determining that a wearer is engaged in a particular activity comprises determining at least one of a pulse rate or a pulse timing based on the first signal.

17. The non-transitory computer-readable medium of claim 13, wherein the particular activity of the wearer is locomotion, and wherein the second sensor comprises at least one of an accelerometer or a gyroscope.

18. The non-transitory computer-readable medium of claim 17, wherein the second body segment is an ankle of the wearer, wherein the one or more discrete events comprise one or more individual footsteps taken by the wearer, and wherein determining a characteristic of each of the one or more discrete events comprises determining a duration of each of the one or more individual footsteps taken by the wearer.

19. The non-transitory computer-readable medium of claim 17, wherein the second body segment is a torso of the wearer, wherein the one or more discrete events comprise one or more discrete turns of the wearer's torso, and wherein determining a characteristic of each of the one or more discrete events comprises determining a mean angular velocity of each of one the or more discrete turns of the wearer's torso.

20. The non-transitory computer-readable medium of claim 13, wherein receiving, from the second sensor, the second signal relating to the second body segment comprises operating a transceiver to receive a wireless indication of the second signal.

* * * * *